(12) United States Patent
Ashenhurst

(10) Patent No.: US 10,729,580 B2
(45) Date of Patent: Aug. 4, 2020

(54) CAPSULAR SPACE CLEARING APPARATUS AND USE THEREOF

(71) Applicant: Michael Edward Ashenhurst, Calgary (CA)

(72) Inventor: Michael Edward Ashenhurst, Calgary (CA)

( * ) Notice: Subject to any disclaimer, the term of this patent is extended or adjusted under 35 U.S.C. 154(b) by 632 days.

(21) Appl. No.: 15/408,040

(22) Filed: Jan. 17, 2017

(65) Prior Publication Data

US 2018/0200107 A1     Jul. 19, 2018

(51) Int. Cl.
| | |
|---|---|
| *A61M 1/00* | (2006.01) |
| *A61F 9/007* | (2006.01) |
| *A61F 9/008* | (2006.01) |

(52) U.S. Cl.
CPC .......... *A61F 9/00736* (2013.01); *A61F 9/007* (2013.01); *A61M 1/0058* (2013.01); *A61F 2009/00887* (2013.01); *A61M 2210/0612* (2013.01)

(58) Field of Classification Search
CPC .................. A61F 9/00736; A61F 9/007; A61F 2009/00887; A61F 9/00727; A61M 1/0058; A61M 2210/0612; A61M 1/0082; A61C 1/05; A61C 1/052; A61C 1/055; Y10S 415/904
See application file for complete search history.

(56) References Cited

U.S. PATENT DOCUMENTS

| | | | | |
|---|---|---|---|---|
| 5,860,994 A | * | 1/1999 | Yaacobi | A61F 9/00754 606/166 |
| 6,030,215 A | * | 2/2000 | Ellion | A46B 11/001 222/324 |
| 6,432,078 B1 | | 8/2002 | Peyman | |
| 6,875,221 B2 | | 4/2005 | Cull | |

(Continued)

FOREIGN PATENT DOCUMENTS

| | | |
|---|---|---|
| DE | 10220253 A1 | 11/2002 |
| WO | 2004039295 A1 | 5/2004 |

OTHER PUBLICATIONS

International Patent Application No. PCT/CA2018/050038, International Search Report and Written Opinion dated Apr. 5, 2018, (9 pages).

(Continued)

*Primary Examiner* — Adam Marcetich
*Assistant Examiner* — Jessica R Arble
(74) *Attorney, Agent, or Firm* — Stephen M. De Klerk

(57) ABSTRACT

An apparatus and use thereof for clearing a capsular space following removal of a cataract or other ophthalmologic procedure. The apparatus includes a body having an irrigation outlet, an aspiration inlet, and a sweeper head rotatably connected with the body for extending a portion of the body including the irrigation outlet, the aspiration inlet, and the sweeper head into the capsular space. The sweeper head is connected with the body by a flow-to-rotary converter located in a cavity within the body for powering the sweeper (Continued)

head with fluid flow while irrigating the capsular space, aspirating the capsular space, or both. Sweeping a surface of the lens capsule while irrigating facilitates clearing remnants and other material from the capsular space following removal of cataracts or another ophthalmologic procedure.

21 Claims, 11 Drawing Sheets

(56) References Cited

U.S. PATENT DOCUMENTS

| | | | |
|---|---|---|---|
| 7,041,078 B1 | 5/2006 | Peyman | |
| 7,976,528 B2 | 7/2011 | Nash et al. | |
| 8,641,658 B1 | 2/2014 | Banko | |
| 2005/0251105 A1* | 11/2005 | Peyman | A61F 9/00736 604/521 |
| 2014/0102445 A1* | 4/2014 | Clement | A61M 25/00 128/202.13 |
| 2014/0114335 A1 | 4/2014 | Banko | |
| 2014/0276369 A1 | 9/2014 | Banko | |
| 2014/0276372 A1 | 9/2014 | Eastman et al. | |
| 2014/0309649 A1* | 10/2014 | Alvarez | A61F 9/00736 606/107 |
| 2015/0025451 A1 | 1/2015 | Banko | |
| 2016/0095679 A1* | 4/2016 | Khakpour | A61O 5/40 433/81 |

OTHER PUBLICATIONS

International Patent Application No. PCT/CA2018/050038, International Preliminary Report on Patentability dated Jul. 23, 2019.

* cited by examiner

CAPSULAR SPACE CLEARING APPARATUS AND USE THEREOF

FIELD

The present disclosure relates generally to clearing the inside of an ocular capsular space in association with an ophthalmologic procedure.

BACKGROUND

Cataracts and other pathologies in an ocular lens are in some cases addressed by removal of some or the entire ocular lens. An eyeball is surrounded by a cornea and a sclera. To access the ocular lens, a corneal incision is made in the cornea, exposing an anterior chamber of the eye. The anterior chamber of the eye is defined posteriorly by the cornea and anteriorly by the lens and the iris. The lens is surrounded by a capsule.

To access the interior of the lens, a capsular incision is made in the capsule to allow access to a capsular space within the capsule. A procedure called continuous curvilinear capsulorhexis may be applied to cut the capsular incision in the capsule. Material from a lens nucleus, where a cataract may form or other pathologies may manifest, may then be removed from the capsule through the capsular incision. The material in the lens, including the cataract, may be broken down, resulting in remnants of cataract and of lens material. The remnants include lens fibers and epithelial cells. The remnants may be removed from the capsular space through the capsular incision by irrigation aspiration or other approaches. A prosthetic lens may then be inserted into the capsular space to replace the material that was removed from the capsular space.

Greater clearing of the remnants from the capsular space is associated with reduced complications following a procedure. Complications may result in reduced vision, may tilt a lens implant, or may result in other problems (e.g. capsule opacification, fibrosis, etc.). It is, therefore, desirable to provide an improved method for clearing the capsular space following a cataract removal or other ophthalmologic procedure.

SUMMARY

It is an object of the present disclosure to obviate or mitigate at least one disadvantage of previous approaches to clearing an ocular capsule. Generally, herein disclosed is a capsular space clearing apparatus and use thereof for clearing a capsular space. The apparatus includes a body sized for insertion into the capsular space through a capsular incision. A sweeper head is rotatably connected with the body for rotation against a surface within the capsular space, such as an anterior leaf or posterior surface of the lens capsule. The sweeper head is rotatably connected with the body by a flow-to-rotary converter, such as a turbine. The sweeper head includes a sweeper surface with material suitable to be rotated against capsular tissue without traumatizing the tissue. The sweeper head may include one or more arms, rods or protrusions, and the sweeper surface may be located at a distal end of each arm, rod or protrusion, the distal end being distal from the body. The flow-to-rotary converter converts fluid flow motion through the body into rotational power for the sweeper head. The body includes apertures and flow paths for irrigating and aspirating the capsular space. The fluid flow may include fluid flow from the body into the capsular space during irrigation, backflow of out of the body for recovery externally to the capsular space, and from the capsular space into the body during aspiration, or a combination thereof. The flow-to-rotary converter may be located between an irrigation flow path and an aspiration flow path to drive the sweeper head by both outflowing irrigation fluid and inflowing aspirated fluid in countercurrent. The flow-to-rotary converter may be located between an irrigation inflow path and irrigation outflow path to drive the sweeper head by both irrigation fluid flowing into the capsular space from the body and out of the body without being provided to the capsular space.

In operation, the body may be inserted through a corneal incision and a capsular incision into a capsular space of a lens capsule following breakdown of a cataract and disruption of fluid and other material within the lens capsule. Fluid flow through the body powers the flow-to-rotary converter, providing rotational power to the sweeper head. The fluid flow may include flow from the body into the capsular space during irrigation, flow into and out of the body during recovery of irrigation fluid, flow from the capsular space into the body during aspiration, or a combination thereof. The irrigation may be continuous and aspiration may be provided when selected by the operator. Sweeping the lens capsule liberates debris remaining after removing the lens and cataract, and facilitates clearing the capsular space and sweeping the surfaces of the capsular space.

The sweeper head may be positioned within the capsule in an anterior position proximate an anterior leaf of the capsule bordering the capsular incision, locating the sweeper surface at and above an equator of the capsule for sweeping an anterior portion of the lens capsule. During rotation of the sweeper head in the anterior position, the sweeper head sweeps the surfaces of the capsule from the anterior leaf to a position proximate the equator of the capsule.

The sweeper head may be positioned within the capsule in a posterior position proximate a posterior surface of the capsule for sweeping a posterior portion of the capsule including the posterior surface of the capsule and capsular surfaces between the posterior surface and the equator. During rotation of the sweeper head in the posterior position, the sweeper head sweeps the surfaces of the capsule from a position proximate the equator of the capsule to the posterior surface.

In a first aspect, herein provided is an apparatus and use thereof for clearing a capsular space following removal of a cataract or other ophthalmologic procedure. The apparatus includes a body having an irrigation outlet, an aspiration inlet, and a sweeper head rotatably connected with the body for extending a portion of the body including the irrigation outlet, the aspiration inlet, and the sweeper head into the capsular space. The sweeper head is connected with the body by a flow-to-rotary converter located in a cavity within the body for powering the sweeper head with fluid flow while irrigating the capsular space, aspirating the capsular space, or both. Sweeping a surface of the lens capsule while irrigating facilitates clearing remnants and other material from the capsular space following removal of cataracts or another ophthalmologic procedure.

In a further aspect, herein provided is a capsular sweeper apparatus comprising: a body extending along a length between a first end and a second end; an irrigation inlet for receiving irrigation fluid into the body; an irrigation outlet proximate the first end and in fluid communication with the irrigation inlet for providing irrigation fluid externally to the body; an aspiration inlet proximate the first end for receiving aspirated fluid into the apparatus; an aspiration outlet in fluid communication with the aspiration inlet for removing aspirated fluid from the apparatus; a sweeper head rotatably connected with the body; a sweeper surface defined on the sweeper head for contacting an ocular capsule during rotation of the sweeper head; and a flow-to-rotary converter engaged with the sweeper head and located within the body for converting flow velocity into rotation velocity to rotate the sweeper head.

In some embodiments, the irrigation outlet is separated from the aspiration inlet along a height perpendicular to the length. In some embodiments, the irrigation outlet is opposite the aspiration inlet along the height.

In some embodiments, the irrigation outlet is proximate the sweeper head along the length.

In some embodiments, the irrigation outlet is proximate to the sweeper head along a height perpendicular to the length.

In some embodiments, the irrigation outlet is defined on a portion of the body overlapping with the sweeper head and in fluid communication with a channel defined in the sweeper head and a sweeper head outlet defined on the sweeper head.

In some embodiments, the irrigation outlet is separated from the sweeper head along the length and proximate the sweeper head along a height perpendicular to the length. In some embodiments, the aspiration inlet is opposite the irrigation outlet along the height.

In some embodiments, the aspiration inlet is defined in the body for receiving the aspirated fluid into the body and the aspiration outlet is defined in the body for removing aspirated fluid from the body.

In some embodiments, the apparatus comprises an aspiration flow conduit connected with and fluidically isolated from the body, and wherein the aspiration inlet is defined in the aspiration flow conduit for receiving the aspirated fluid into the aspiration flow conduit and the aspiration outlet is defined in the aspiration flow conduit for removing aspirated fluid from the aspiration flow conduit.

In some embodiments, the aspiration outlet is proximate to the sweeper head along a height perpendicular to the length.

In some embodiments, the sweeper head comprises a hub and at least one protrusion extending from the hub, and the sweeper surface is located on the at least one protrusion. In some embodiments, the at least one protrusion comprises at least two arms extending from the sweeper hub. In some embodiments, the at least one protrusion extends from a portion of the hub distal from the body. In some embodiments, the at least one protrusion extends from a lateral portion of the hub. In some embodiments, the at least one protrusion extends from an outer distal portion of the hub.

In some embodiments, the flow-to-rotary converter is located within an irrigation flow path defined in the body between the irrigation inlet and the irrigation outlet for converting flow velocity of fluid in the irrigation flow path into rotation velocity to rotate the sweeper head. In some embodiments, the flow-to-rotary converter is located within an aspiration flow path defined in the body between the aspiration inlet and the aspiration outlet for converting flow velocity of fluid in the aspiration flow path into rotation velocity to rotate the sweeper head. In some embodiments, the flow-to-rotary converter is located within the aspiration flow path in countercurrent with the irrigation flow path. In some embodiments, a cross-sectional surface area of the aspiration flow path is greater than a cross-sectional area of the irrigation flow path for mitigating flow limitation of flow into the body at the aspiration inlet and clogging of the apparatus. In some embodiments, the apparatus comprises a wall within the body for fluidically separating the irrigation flow path from the aspiration flow path. In some embodiments, the flow-to-rotary converter is located within the wall and is in fluid communication with the irrigation flow path and the aspiration flow path.

In some embodiments, the flow-to-rotary converter is located within an irrigation flow path defined in the body between the irrigation inlet and the irrigation outlet for converting flow velocity of fluid in the irrigation flow path into rotation velocity to rotate the sweeper head. In some embodiments, the apparatus includes a wall within the body for fluidically isolating the irrigation flow path from an aspiration flow path defined in the body between the aspiration inlet and the aspiration outlet and wherein the flow-to-rotary converter is located in the body in fluid communication with the irrigation flow path and not with the aspiration flow path. In some embodiments, the apparatus includes a wall within the body for fluidically separating the irrigation flow path into an irrigation inflow path between the irrigation inlet and the irrigation outlet, and an irrigation outflow path between the irrigation outlet and an irrigation recovery outlet. In some embodiments, the flow-to-rotary converter is located within the wall and is in countercurrent fluid communication with the irrigation inflow path and the irrigation outflow path. In some embodiments, the apparatus includes an aspiration flow conduit connected with the body and fluidically isolated from the irrigation flow path, and wherein the aspiration inlet is defined in the aspiration flow conduit for receiving the aspirated fluid into the aspiration flow conduit and the aspiration outlet is defined in the aspiration flow conduit for removing aspirated fluid from the aspiration flow conduit. In some embodiments, a cross-sectional surface area of the aspiration inlet is greater than a cross-sectional area of the irrigation flow path for mitigating flow limitation of flow into the body at the aspiration inlet and clogging of the apparatus.

In some embodiments, the flow-to-rotary converter is located within an aspiration flow path between the aspiration inlet and the aspiration outlet for converting flow velocity in the aspiration flow path into rotation velocity to rotate the sweeper head.

In some embodiments, the flow-to-rotary converter comprises a turbine.

In a further aspect, herein provided is a method of clearing debris from a capsular space within a lens capsule, the method comprising: positioning a capsular sweeping apparatus within the lens capsule; irrigating the capsular space through the capsular sweeping apparatus; aspirating the capsular space through the capsular sweeping apparatus; and applying fluid flow through the capsular sweeping apparatus to rotate a sweeper head of the capsular sweeping apparatus against a surface of the capsular space for clearing debris from the capsular space.

In some embodiments, the fluid flow comprises irrigation fluid flow. In some embodiments, the fluid flow comprises aspirated fluid flow. In some embodiments, applying the fluid flow to rotate the sweeper head comprises providing the irrigation fluid flow in countercurrent with aspirated fluid flow. In some embodiments, the irrigation fluid flow comprises irrigation fluid inflow in countercurrent with irrigation fluid outflow.

In some embodiments, the fluid flow comprises aspirated fluid flow. In some embodiments, the fluid flow comprises irrigation fluid flow. In some embodiments, applying fluid flow to rotate the sweeper head comprises providing the aspirated fluid flow in countercurrent with the irrigation fluid flow.

In some embodiments, positioning the capsular sweeping apparatus within the lens capsule comprises positioning the capsular sweeping apparatus within an anterior portion of the lens capsule and the surface comprises a portion of the lens capsule extending between an anterior leaf of the lens capsule and an equator of the lens capsule.

In some embodiments, positioning the capsular sweeping apparatus within the lens capsule comprises positioning the capsular sweeping apparatus within a posterior portion of the lens capsule and the surface comprises a posterior surface of the lens capsule.

In a further aspect, herein provided is use of a capsular sweeper apparatus for clearing debris from a capsular space of a lens capsule, the apparatus being configured for location within the lens capsule, irrigation of the capsular space, and aspiration of the capsular space, and wherein a sweeper head of the apparatus is configured for rotation against a surface of the capsular space for clearing debris from the capsular space when a fluid flow is applied through the apparatus.

In some embodiments, the fluid flow comprises irrigation fluid flow. In some embodiments, the fluid flow comprises aspirated fluid flow. In some embodiments, the irrigation fluid is in countercurrent with aspirated fluid flow. In some embodiments, the irrigation fluid flow comprises irrigation fluid inflow in countercurrent with irrigation fluid outflow.

In some embodiments, the fluid flow comprises aspirated fluid flow. In some embodiments, the fluid flow comprises irrigation fluid flow. In some embodiments, the fluid flow comprises aspirated fluid flow in countercurrent with irrigation fluid flow.

In some embodiments, the apparatus is configured for location within an anterior portion of the lens capsule and the surface comprises a portion of the lens capsule extending between an anterior leaf of the lens capsule and an equator of the lens capsule.

In some embodiments, the apparatus is configured for location within a posterior portion of the lens capsule and the surface comprises a posterior surface of the lens capsule.

In a further aspect, herein provided is use of any capsular sweeper apparatus described herein for removal of debris from a capsular space within a lens capsule.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached figures, in which features sharing reference numerals with a common final two digits of a reference numeral correspond to similar features across multiple figures (e.g. the body 12, 112, 212, 312, 412, 512, 612, etc.).

DETAILED DESCRIPTION

Figure 1:
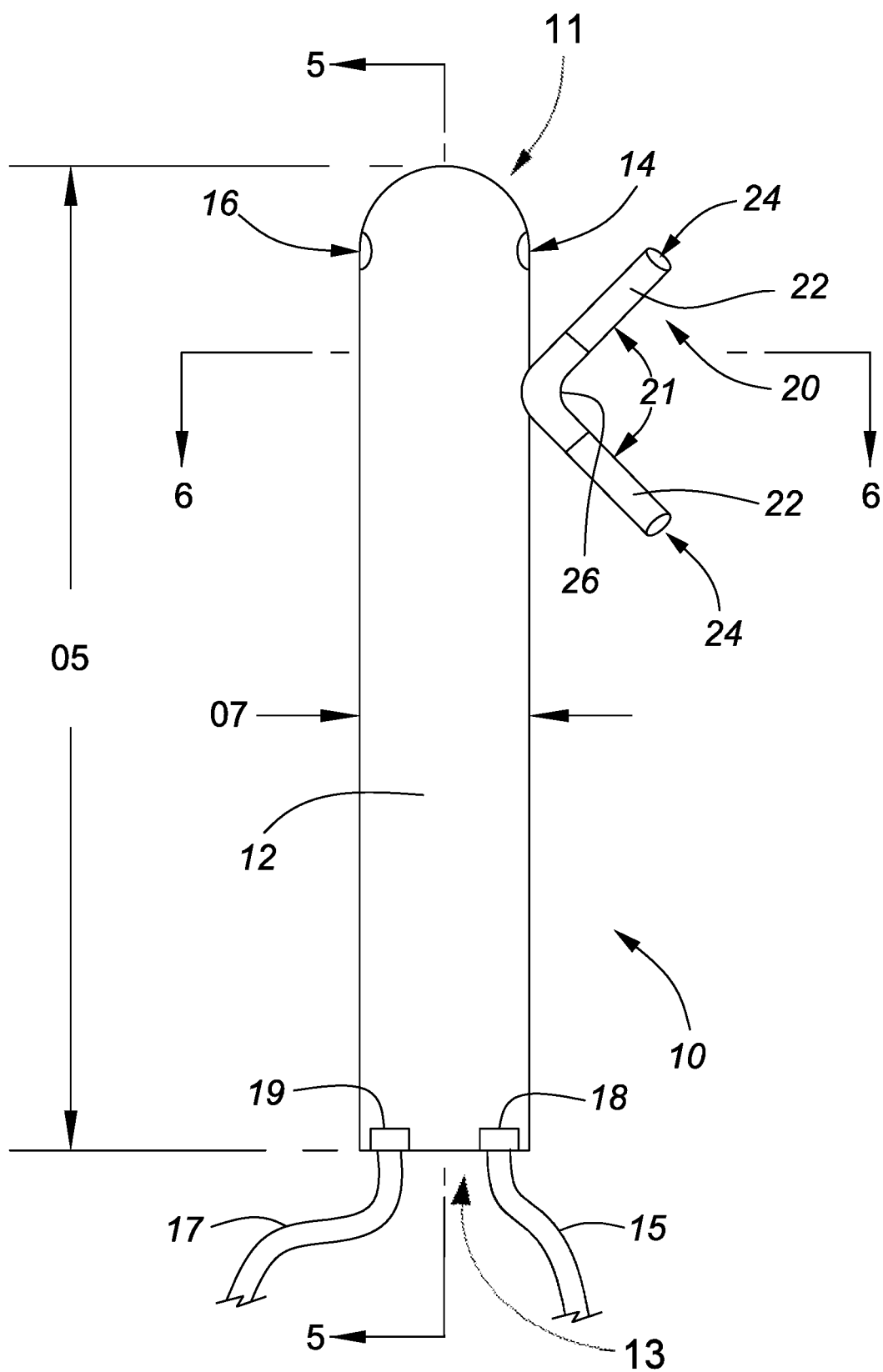
FIG. 1 is a perspective view schematic of a capsular space clearing apparatus.
Figure 2:
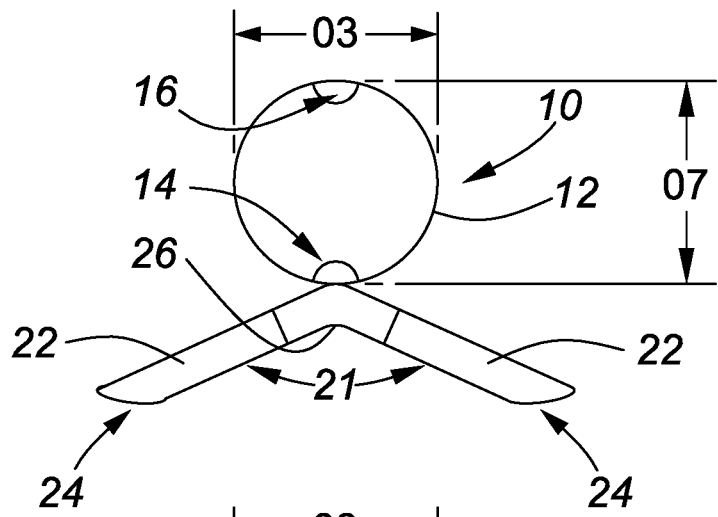
FIG. 2 is an elevation view schematic of the apparatus of FIG. 1.
Figure 3:
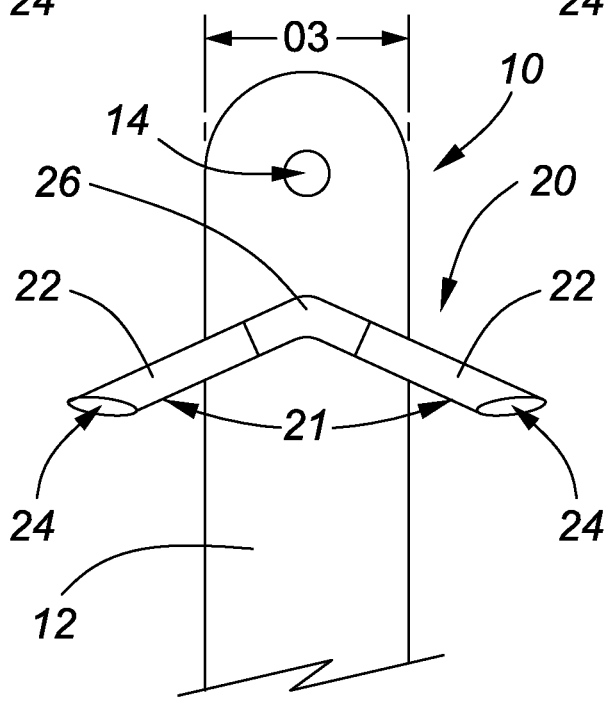
FIG. 3 is a bottom plan view schematic of the apparatus of FIG. 1.
Figure 4:
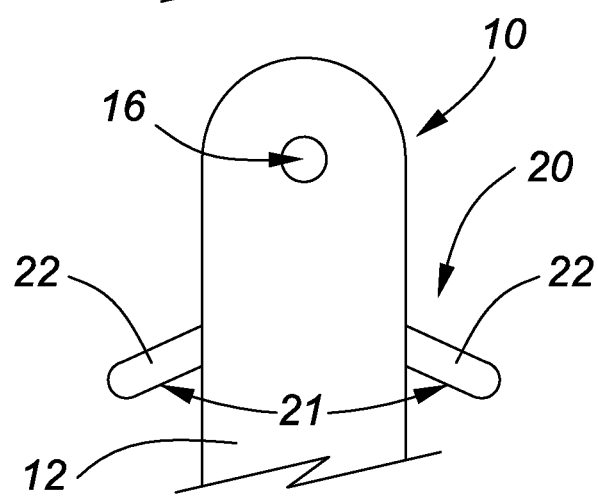
FIG. 4 is a top plan view schematic of the apparatus of FIG. 1.

Generally, the present disclosure provides an apparatus and method for clearing an ocular capsule, and use of a capsular sweeper apparatus for clearing debris from a capsular space of a lens capsule. A capsular space clearing apparatus includes a body sized for insertion into a capsular space through a capsular incision. A cavity is defined within the body. An irrigation flow path within the cavity provides fluid communication with an irrigation outlet for irrigating the capsular space. An aspiration flow path within the cavity provides fluid communication with an aspiration inlet aspirating the capsular space. A sweeper head is rotatably connected with the body for rotation against a surface within the capsular space, such as an anterior leaf or posterior surface of the capsule. The sweeper head is rotatably connected with the body by a flow-to-rotary converter, such as a turbine.

The sweeper head includes a sweeping surface with material suitable to be rotated against capsular tissue without traumatizing the tissue. The sweeper surface of the sweeper head may be a single continuous surface or may be distributed among two or more arms, rods or other sweeper protrusions. The sweeper head may include a hub with the sweeper protrusions extending from the hub or the sweeper surface may be defined by a portion of the hub. The sweeper head may be located proximate the irrigation outlet, and may overlap with the irrigation outlet.

The flow-to-rotary converter converts fluid flow motion through at least one of the flow paths into rotational power for the sweeper head. Rotation of the sweeper head allows the sweeper surface to sweep against tissue of the lens capsule for clearing debris following a cataract removal or other procedure. The fluid flow may include fluid flow from the body into the capsular space during irrigation, from the capsular space into the body during aspiration, or both. The flow-to-rotary converter may be located between the irrigation flow path and the aspiration flow path to drive the sweeper head by both outflowing irrigation fluid and inflowing aspirated fluid in countercurrent. The flow-to-rotary converter may be located between inflowing and outflowing portions of the irrigation flow path to drive the sweeper head by both inflowing irrigation fluid flowing from the body into the ocular cavity through the irrigation outlet, and by outflowing irrigation fluid flowing out of the body in countercurrent to the inflowing irrigation fluid and back to a recovery outlet rather than to the irrigation outlet.

The body may have an elongate shape extending between a first end and an opposed second end. The sweeper head may be located proximate the first end for inserting into the capsular space and a handle may be located proximate the second end for manipulating the body while inserting the first end of the body into the capsular space.

The irrigation outlet may be located proximate the sweeper head and the first end for providing irrigation fluid (e.g. balanced salt solution ("BSS"), etc.) to the capsular space during and in close proximity to sweeping. An irrigation inlet provides fluid communication from a source of irrigation fluid, through the irrigation flow path, and to the irrigation outlet. The irrigation inlet may be located proximate the second end for providing irrigation fluid into the body. Where the apparatus includes the recovery outlet for recovering irrigation fluid flowing through the body but not out into the ocular cavity, the recovery outlet may be located proximate the second end.

The aspiration inlet may be located proximate the first end for removing aspirated fluid (e.g. BSS or other fluid mixed with debris left in in the capsular space following a procedure, etc.) from the capsular space. An aspiration outlet provides fluid communication from the aspiration inlet, through the aspiration flow path, and to an aspiration fluid receptacle in fluid communication with the aspiration outlet for recovering aspirated fluid from the body for disposal. A source of negative pressure may be applied to the aspiration outlet from the aspiration fluid receptacle or otherwise for aspiration. The aspiration outlet may be located proximate the second end for facilitating connection with the aspiration fluid receptacle and the source of negative pressure.

The irrigation outlet and the aspiration inlet may be located separately from each other and also each proximate the first end for providing irrigation fluid and aspirating aspirated fluid at separate portions of the body proximate the first end. The irrigation outlet and the aspiration inlet may be separated from each other along a height of the body, the height being perpendicular to a length of the body, the length extending between the first end and the second end. Where the body is generally cylindrical, the irrigation outlet and the aspiration inlet may be radially distal from each other and axially proximate each other.

In operation, the apparatus may be used to clear a capsular space within a lens capsule after breakdown of a cataract and disruption of fluid and other material within the lens capsule. The first end of the body may be inserted through a corneal incision in a cornea and a capsular incision in the lens capsule, and into the capsular space of a lens capsule. Fluid flow through the cavity powers the flow-to-rotary converter, providing rotational power to the sweeper head. The fluid flow may include flow through the irrigation flow path and into the capsular space through the irrigation outlet during irrigation of the capsular space. The fluid flow may include flow through the aspiration flow path and into the aspiration receptacle through the aspiration outlet during aspiration. Flow through the irrigation flow path may be continuous and aspiration may be provided when selected by the operator.

Sweeping the lens capsule liberates debris remaining after removing the lens and cataract, and facilitates clearing the capsular space of surfaces of the lens capsule. During sweeping, the apparatus may be positioned within the capsule in an anterior position relative to the capsular space or a posterior position relative to the capsular space.

The anterior position may locate the sweeper head proximate an anterior leaf of the capsule bordering the capsular incision. During rotation of the sweeper head with the apparatus in the anterior position, the sweeper head sweeps the surfaces of the capsule from the anterior leaf to a position proximate an equator of the lens capsule.

The posterior position may locate the sweeper head proximate a posterior surface of the lens capsule for sweeping the posterior surface and surfaces of the lens capsule between the posterior surface and the equator. During rotation of the sweeper head in the posterior position, the sweeper head sweeps surfaces of the capsule from a portion of the lens capsule proximate the equator to a posterior surface of the lens capsule.

FIGS. 1 to 4 show a capsular space sweeper apparatus 10. The apparatus 10 includes a body 12 extending along a length 05 between a first end 11 and a second end 13. A width 03 and a height 07 are each perpendicular to the length 05.

Figure 9:
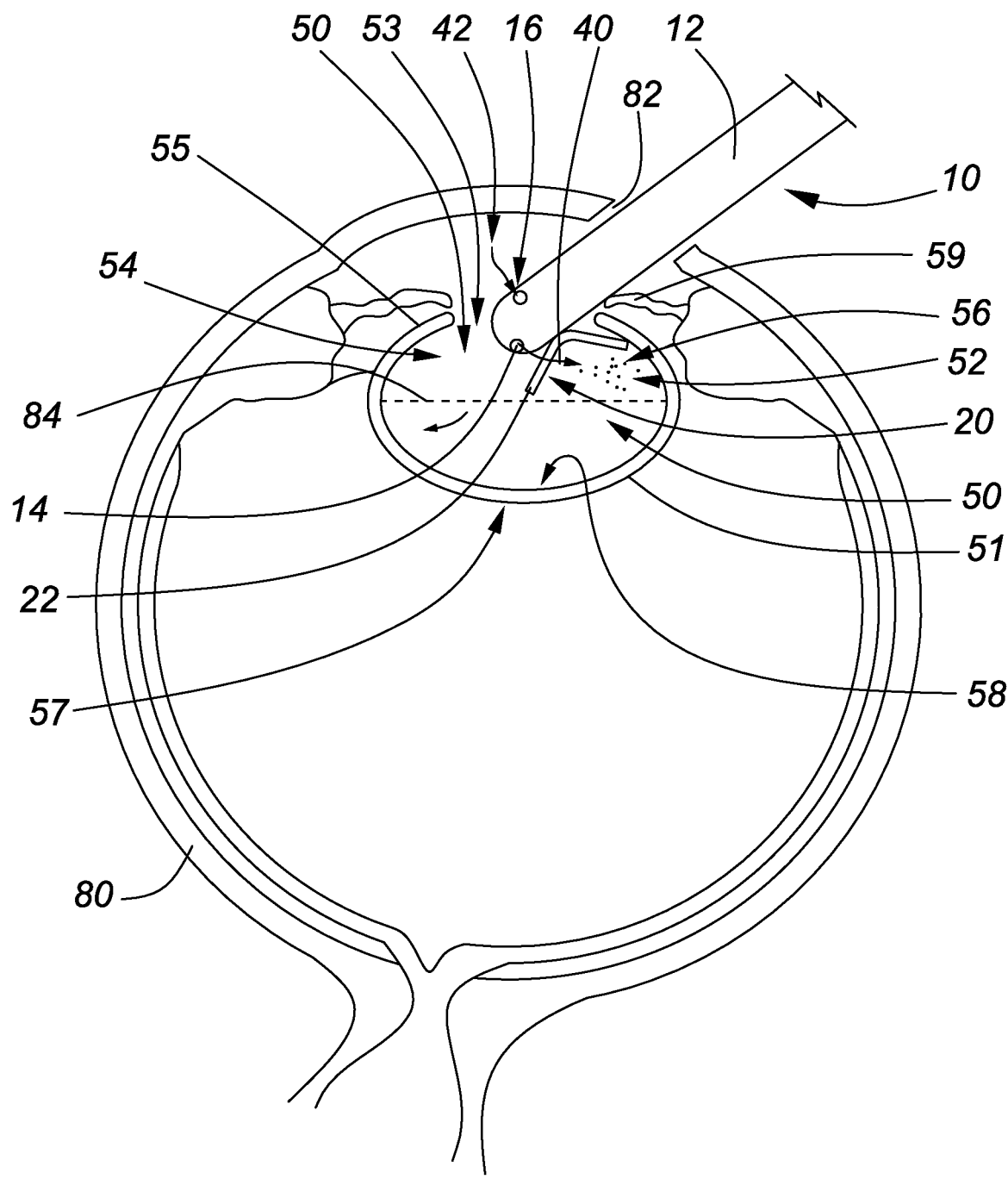
FIG. 9 is a schematic of the apparatus of FIG. 1 located in an anterior position of the lens capsule and in use to clear an anterior leaf and an anterior portion of a capsular space in a lens capsule.
Figure 10:
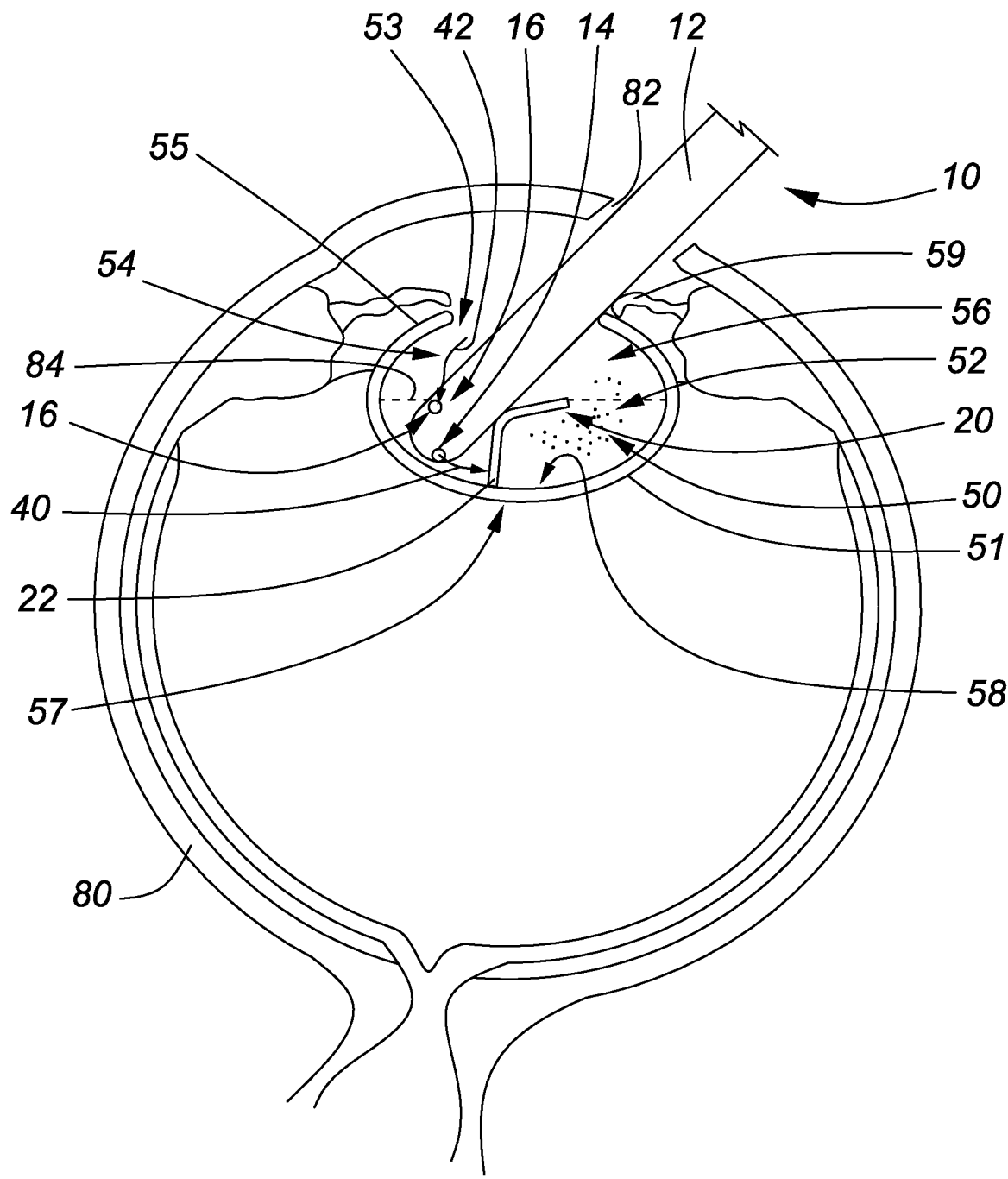
FIG. 10 is a schematic of the apparatus of FIG. 1 located in a posterior position of the lens capsule and in use to clear a posterior surface and a posterior portion of a capsular space in a lens capsule.

An irrigation outlet 14 is defined in the body 12 proximate the first end 11 for providing irrigation fluid (e.g. BSS, etc.) to a capsular space of a lens capsule, such as the capsular space 50 shown in FIGS. 9 and 10. An aspiration inlet 16 is defined in the body 12 proximate the first end 11 for receiving aspirated fluid from within the capsular space. The irrigation outlet 14 and the aspiration inlet 16 may each be located proximate the first end 11 along the length 05 for inserting both the irrigation outlet 14 and the aspiration inlet 16 into a lens capsule at the same time. The irrigation outlet 14 and the aspiration inlet 16 may each be located proximate a center of the body 12 along the width 05. The irrigation outlet 14 and the aspiration inlet 16 may be located opposite each other along the height 07 for providing irrigation fluid in a posterior direction relative to a lens capsule within which the apparatus 10 is located while recovering aspirated fluid in an anterior direction (see FIGS. 9 and 10).

An irrigation inlet 18 is defined in the body 12 proximate the second end 13 and is in fluid communication with the irrigation outlet 14 for providing irrigation fluid to the body 12 and the irrigation outlet 14. An aspiration outlet 19 is defined in the body 12 proximate the second end 13 and is in fluid communication with the aspiration inlet 16 for applying negative pressure to the aspiration inlet 16 while recovering aspirated fluids flowing into the aspiration inlet 16 from within the capsular space and through the body 12.

The irrigation outlet 14 and the aspiration inlet 16 may be located proximate the first end 11 longitudinally along the length 05 but otherwise separated from each other about the body 12 for balancing irrigation of the capsular space with aspiration of the capsular space, such as opposed from one another across the height 07. The body 12 is shown with the general shape of a cylinder with a circular radial cross-section, in which case the irrigation outlet 14 and aspiration inlet 16 may be spaced radially distally from each other along the height 07 for balancing irrigation and aspiration but located axially proximate each other and axially proximate the first end 11. Where the body is not cylindrical or otherwise generally circular in cross-section, the irrigation outlet and the aspiration inlet may be spaced longitudinally proximate each other along the length and distally from each other along the height, the width, or otherwise on a cross-sectional area of the body corresponding to a radial cross-sectional area in the body 12.

An irrigation connection 15 may be connected with the irrigation inlet 18 for supplying irrigation fluid to the apparatus 10. An aspiration connection 17 may be connected with the aspiration outlet 19 for supplying negative pressure to the apparatus 10 to balance delivery of irrigation fluid to the capsular space and to recover aspirated fluid from the capsular space. Aspirated fluid may include irrigation fluid and any fluid or debris recovered from the capsular space.

A sweeper head 20 is rotatably connected with the body 12 proximate the first end 11. The sweeper head 20 may include a hub 26 and a pair of arms 22 extending from the hub 26. The arms 22 may be used to sweep one or more surfaces of the capsule when the sweeper head 20 is positioned against a surface of the capsule or within the capsule and rotated against the capsule. The arms 22 may include tapered tips 24 and may be prepared from semi-rigid silicone or any suitable sweeper material that provides a sweeper surface for mitigating trauma to the capsule tissue resulting from rotation of the arms 22 against the capsule tissue.

The arms 22 may be separated by an angle 21 and generally arranged in a "V" configuration to facilitate insertion of the apparatus 10 into, and removal of the apparatus 10 from, a capsulorhexis through which the apparatus 10 is inserted for use in clearing a capsular space. The angle 21 may be between about 120° and about 150°. The arms 22 may extend about 5 mm from the hub 26. The sweeper head 20 may extend from the body 12 proximate the irrigation outlet 14 for irrigating the capsular space in close association with sweeping surfaces of the capsular space.

Figure 5:
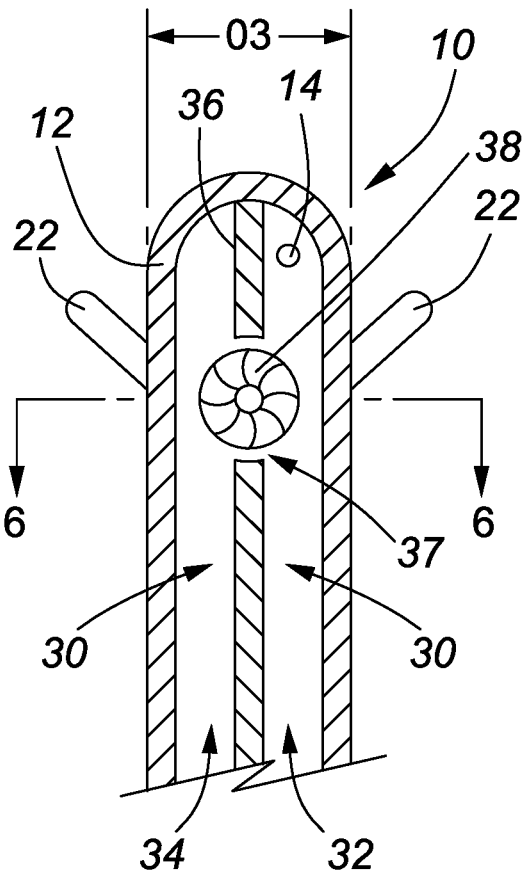
FIG. 5 is a cross-sectional plan view schematic of the apparatus of FIG. 1 along the 5-5 section.
Figure 6:
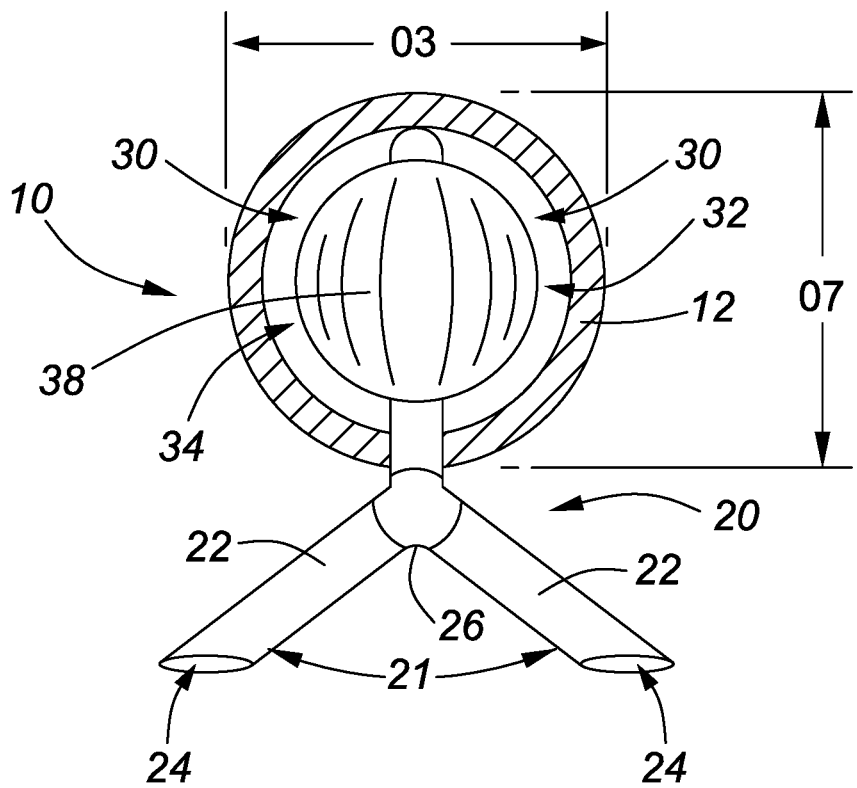
FIG. 6 is a cross-sectional schematic plan view of the apparatus of FIG. 1 along the 6-6 section.

FIGS. 5 and 6 show cross-sections of the apparatus 10 along the cross-sectional axes defined in FIGS. 1 and 5, respectively. A cavity 30 is defined within the body 12. The cavity 30 is divided into an irrigation flow path 32 and an aspiration flow path 34. The cross-sectional surface area of the aspiration inlet 16 may be greater than the cross-sectional area of the irrigation flow path 32 to mitigate limiting the flow at the aspiration inlet 16 and clogging of the apparatus 10. Similarly, the cross-sectional surface area of the aspiration flow path 34 may be than the cross-sectional area of the irrigation flow path 32 to mitigate limiting the flow at the aspiration inlet 16 and clogging of the apparatus 10. A wall 36 fluidically separates the irrigation flow path 32 from the aspiration flow path 34 other than at a gap 37. A turbine 38 is located in the gap 37 between the irrigation flow path 32 and the aspiration flow path 34.

Figure 7:
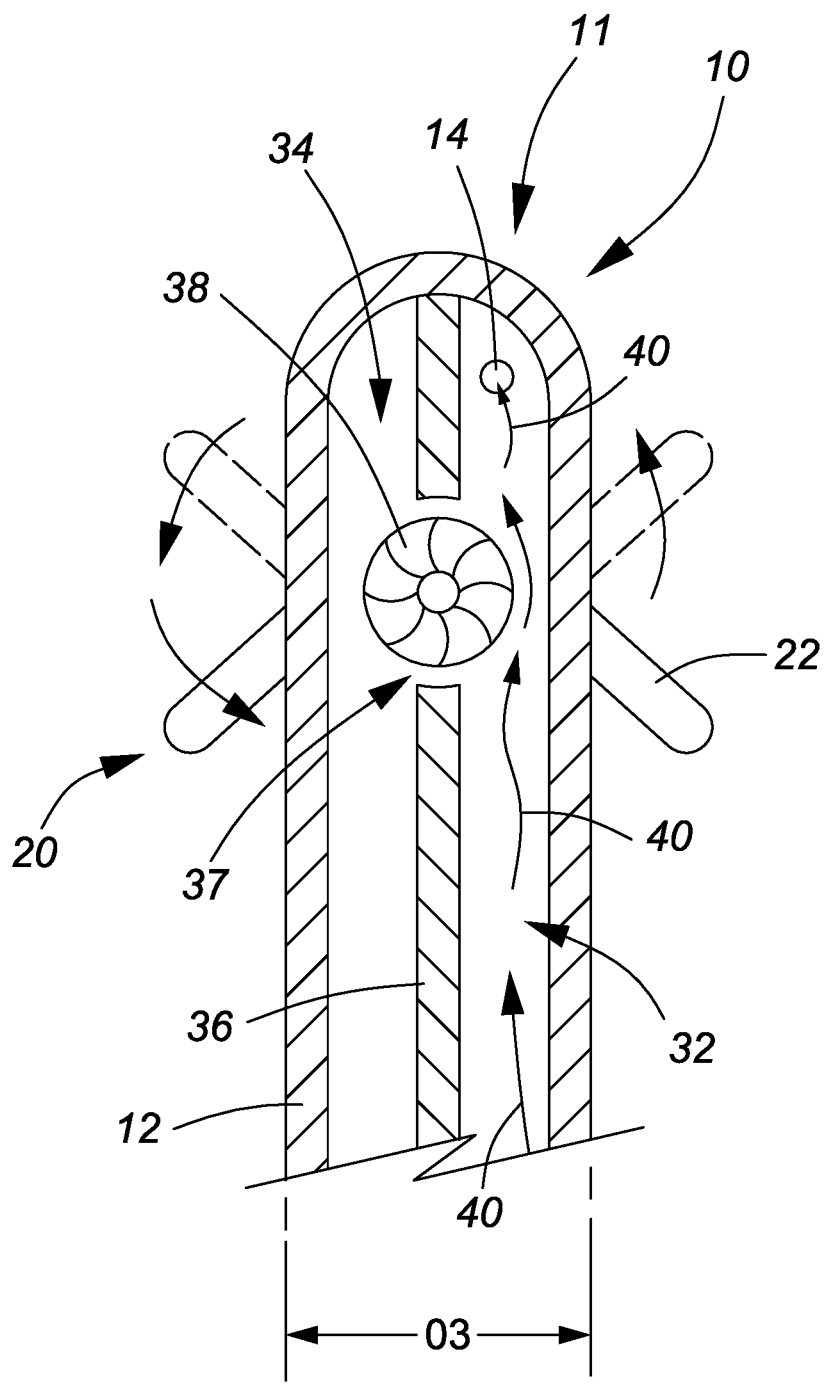
FIG. 7 is a cross-sectional schematic plan view of the apparatus of FIG. 1 along the 5-5 section during operation and irrigation of a lens capsule.

FIG. 7 shows a cross-section of the body 12 during flow of irrigation fluid 40 from the irrigation inlet 18 through the irrigation flow path 32 to the irrigation outlet 14 for providing irrigation fluid 40 to the capsular space. Flow of irrigation fluid 40 along and through the turbine 38 rotates the sweeper head 20 while also providing irrigation fluid 40 to the capsular space through the irrigation outlet 14 during rotation of the sweeper head 20.

Figure 8:
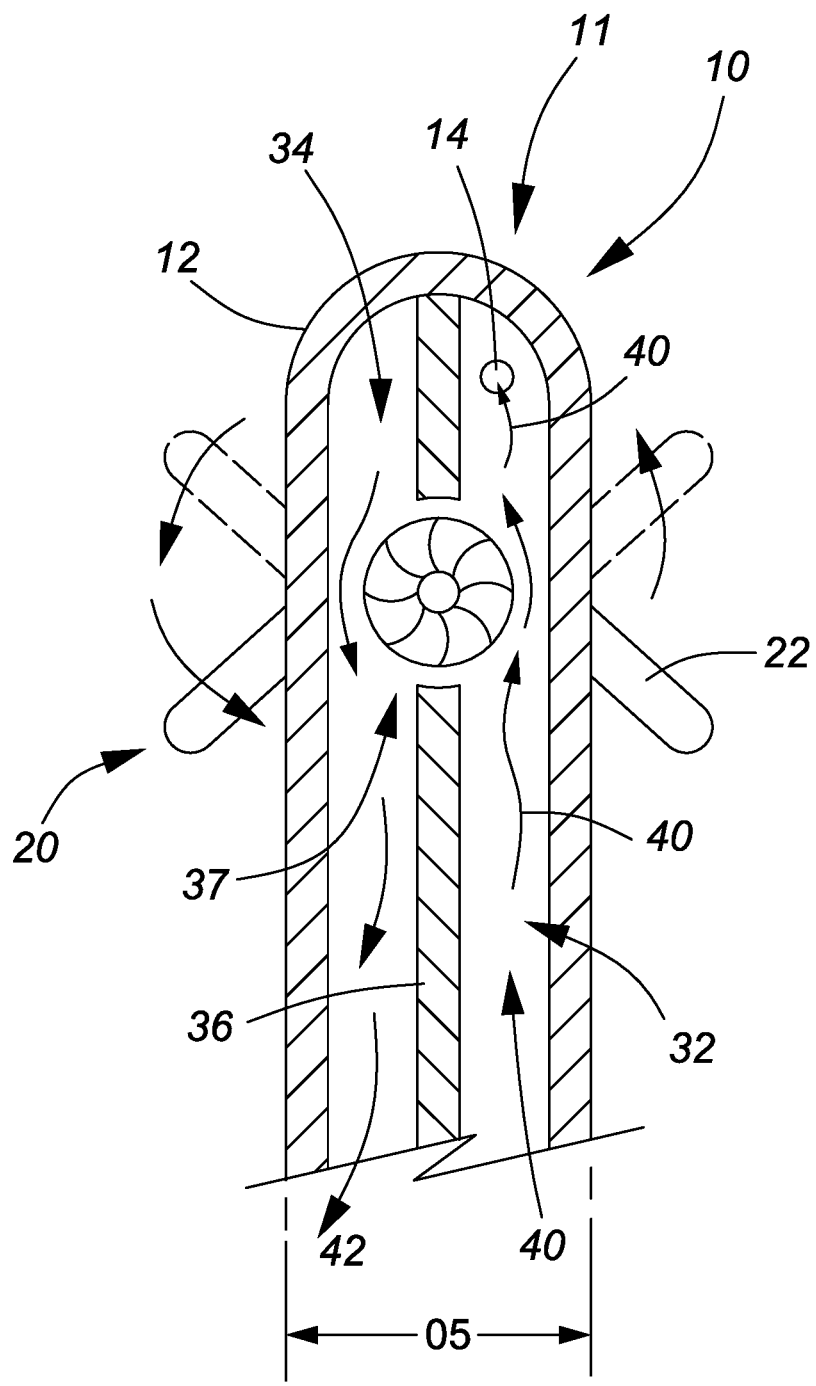
FIG. 8 is a cross-sectional schematic plan view of the apparatus of FIG. 1 along the 5-5 section during operation, irrigation, and aspiration of a lens capsule.

FIG. 8 shows a cross-section of the body 12 during flow of irrigation fluid 40 from the irrigation inlet 18 through the irrigation flow path 32 to the irrigation outlet 14 for providing irrigation fluid 40 to the capsular space. Flow of irrigation fluid 40 along and through the turbine 38 rotates the sweeper head 20 while also providing irrigation fluid 40 to the capsular space through the irrigation outlet 14 during rotation of the sweeper head 20. Inflow of aspirated fluid 42 from a capsular space balances the fluid flow and facilitates driving of the turbine 38. The aspirated fluid 42 may include a mixture of irrigation fluid, endogenous fluid from the capsular space, fragments of lens capsule, fragments of cataracts, and remnants. Aspirated fluid 42 flows into the body 12 through the aspiration inlet 16 (see FIGS. 9 and 10), through the aspiration flow path 34, and out of the body 12 through the aspiration outlet 19.

FIGS. 9 and 10 show the apparatus 10 being used to clear a capsular space 50 within a lens capsule 51 in which a capsulorhexis 53 has been cut. The lens capsule 51 is posterior to an iris 59 and within a cornea 80 into which a corneal incision 82 has been cut. Remnants 52 within the capsular space 50 are mixed with irrigation fluid 40 from the irrigation outlet 14, resulting in aspirated fluid 42, which is removed from the capsular space 50 by aspiration into the aspiration inlet 16. During clearing, irrigation fluid 40 may be delivered continuously to the capsular space 50 through delivery of irrigation fluid 40 to the irrigation outlet 14. The sweeper head 20 may be rotated against a lens surface 58 of the lens capsule 51 during irrigation for sweeping the lens capsule 51.

In FIG. 9, the apparatus 10 is shown providing irrigation fluid 40 to the capsular space 50 and recovering aspirated fluid 42 from the capsular space 50. As shown in FIG. 7, irrigation fluid 40 may be provided to the capsular space 50 without aspiration of aspirated fluid 42 from the capsular space 50. As shown in FIG. 8, irrigation fluid 40 may be provided to the capsular space 50 in combination with aspiration of aspirated fluid 42 from the capsular space 50 by selective activation of negative pressure on the aspiration flow path 34 and the aspiration outlet 16 as necessary to clear the aspirated fluid 42. Outflow of irrigation fluid 40 from the body 12 and inflow of aspirated fluid 42 into the body 12 may both contribute to driving the sweeper head 20.

In FIG. 9, the apparatus 10 is used to clear an anterior portion 54 of the capsular space 50, including an anterior leaf 55 of the lens capsule 51. By holding the apparatus 10 with the first end 11 of the body 12 positioned proximate the anterior leaf 55, the sweeper head 20 may be positioned with the tapered tips 24 of the arms 22 against the lens surface 58 along the anterior leaf 55. When the sweeper head 20 is rotated through 360 degrees, the lens surface 58 of the lens capsule 51 may be swept from the anterior leaf 55 to an equator 84 of the lens capsule 51, clearing the anterior portion 54 of the remnants 52.

In FIG. 10, the apparatus 10 is used to clear a posterior portion 56 of the capsular space 50, including the lens surface 58 along a posterior end 57 of the lens capsule 51. By holding the apparatus 10 with the sweeper head 20 against the posterior end 57, the sweeper head 20 may be rotated through 360 degrees around the lens surface 58 along the posterior end 57, sweeping the posterior portion 56 of the remnants 52.

Figure 11:
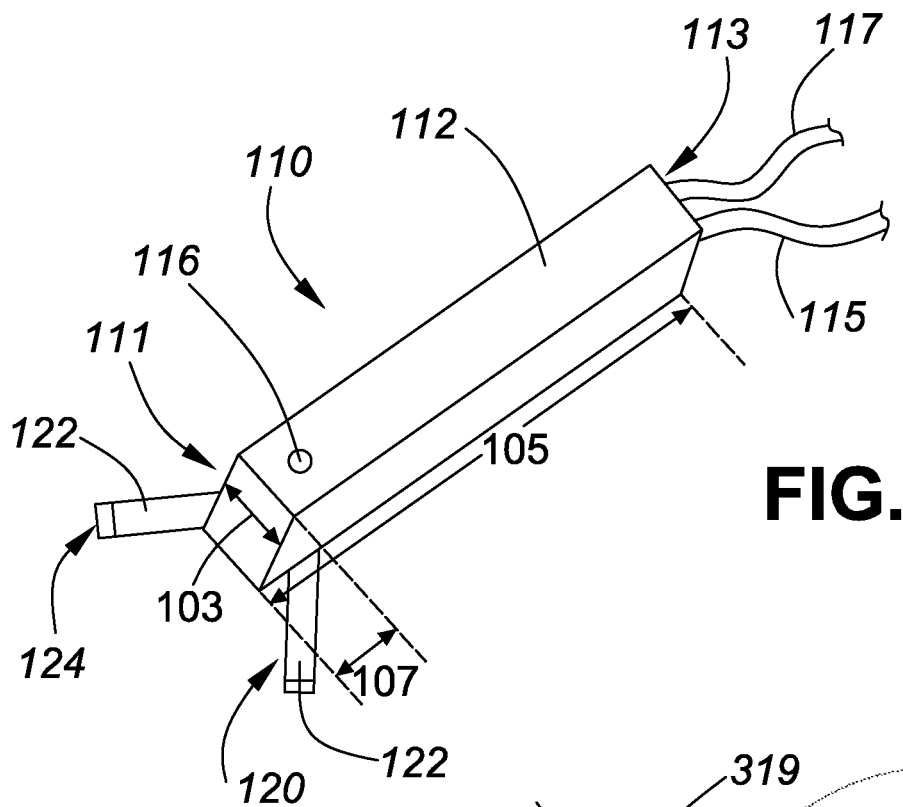
FIG. 11 is a perspective view schematic of a capsular space clearing apparatus.

FIG. 11 shows an apparatus 110 in which the body 112 has a square cross-sectional area, where the body 12 has a circular cross-sectional area. The apparatus 110 otherwise includes similar features to the apparatus 10 shown in FIGS. 1 to 10, including aspiration outlet 116. The body 112 extends along the length 105 between the first end 111 and the second end 113. The sweeper head 120 including the sweeper arms 122 ending in the tapered tips 124 may be located proximate the first end 111. The width 103 and the height 107 are each perpendicular to the length 105. The irrigation connection 115 and the aspiration connection 117 are connected with the body 112 proximate the second end 113. The internal features of the apparatus 110 may be similar to internal features of the apparatus 10 shown in FIGS. 5 and 6, the internal features of the apparatus 210 shown in FIG. 11, the internal features of the apparatus 310 shown in FIG. 12, or any suitable arrangement of internal features.

Figure 12:
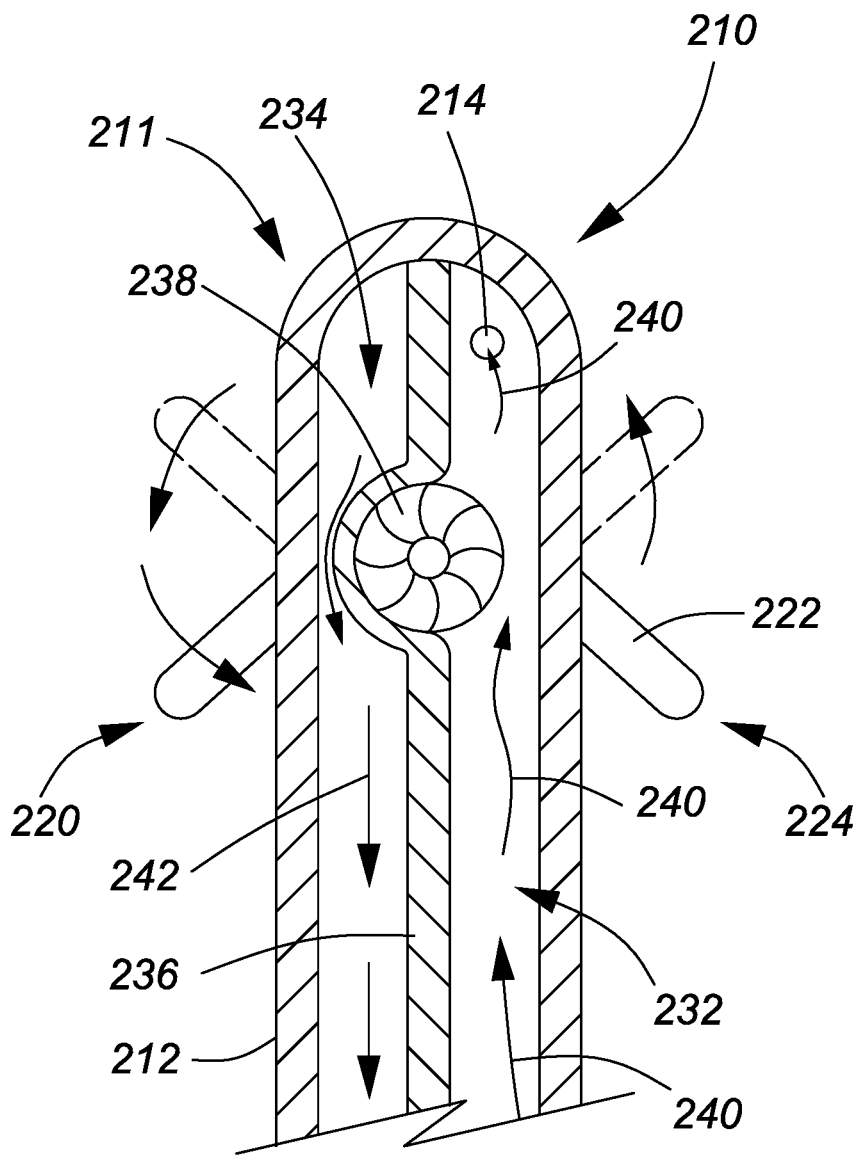
FIG. 12 is a cross-sectional plan view schematic of a capsular space clearing apparatus in operation.

FIG. 12 shows an apparatus 210 in operation. The flow-to-rotary converter 238 is powered by irrigation fluid 240 and not by aspirated fluid 242. This may provide less power to the sweeper head 220 compared with the apparatus 10 or other embodiments in which both irrigation fluid and aspirated fluid power the flow-to-rotary converter. Providing power to the sweeper head 220 by the irrigation flow path 232 but not by the aspiration flow path 234 may facilitate maintaining flow of irrigation fluid at a consistent rate relative to embodiments in which intermittent aspiration fluid also flows through the flow-to-rotary converter, such as in the apparatus 10. The wall 236 extends around the flow-to-rotary converter 238 and fluidically isolates the irrigation flow path 232 from the aspiration flow path 234. The sweeper head 220, which includes the sweeper arms 222 terminating in the tapered ends 224, is located proximate the first end 211. Irrigation outlet 214 is depicted.

Figure 13:
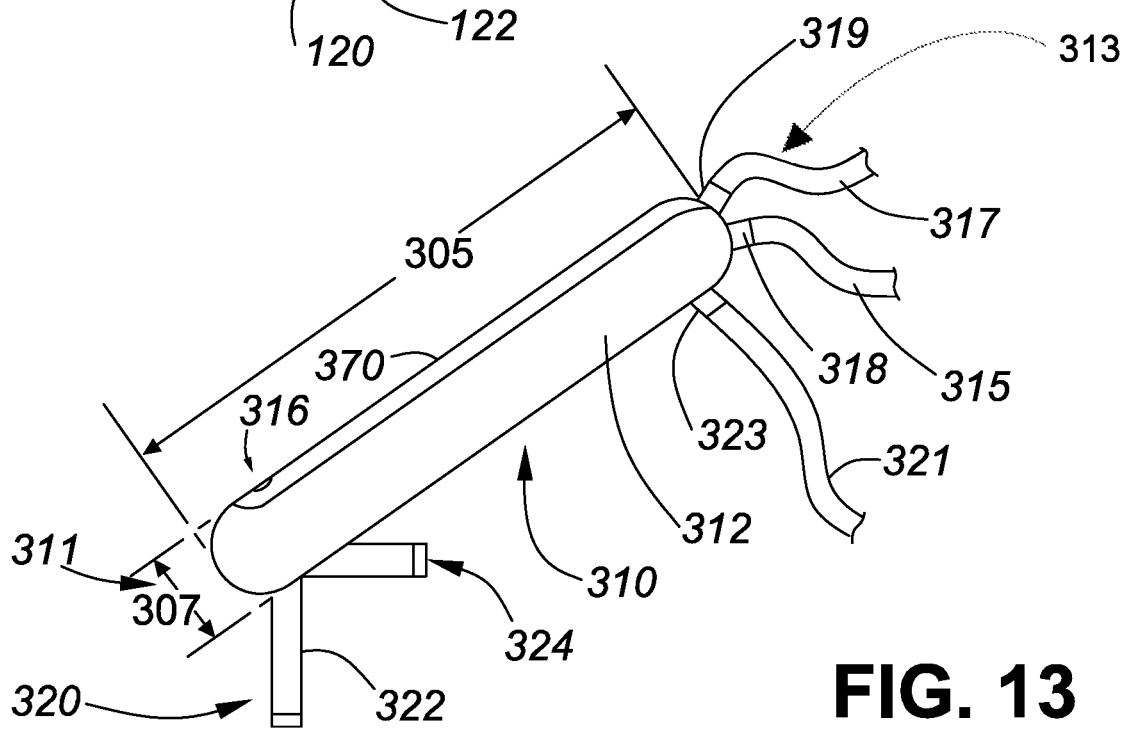
FIG. 13 is a perspective plan view schematic of a capsular space clearing apparatus.
Figure 14:
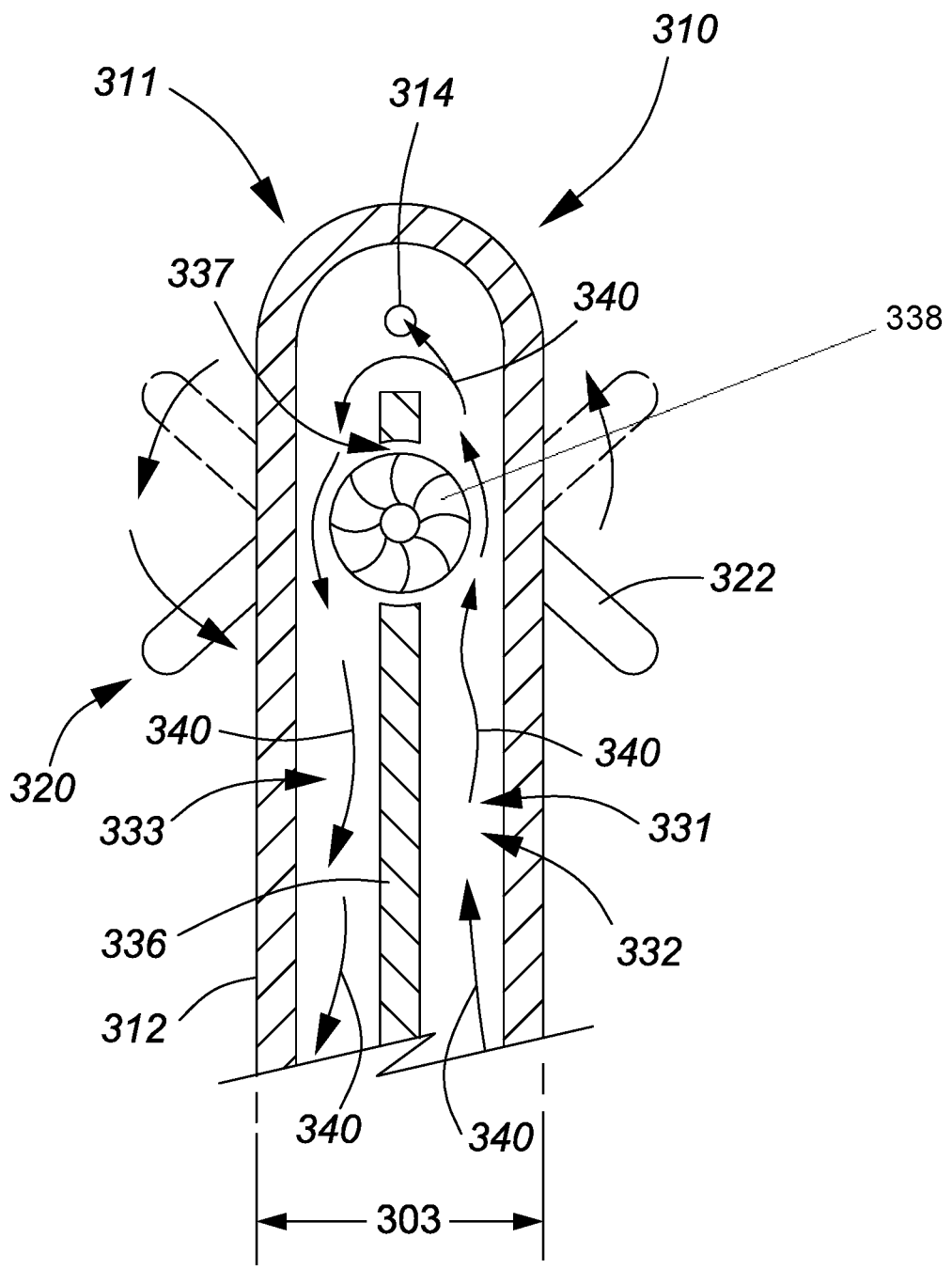
FIG. 14 is a cross-sectional plan view schematic of the apparatus of FIG. 13 during operation and irrigation of a lens capsule.

FIG. 13 shows an apparatus 310. FIG. 14 shows the apparatus 310 in operation. The irrigation flow path 332 extends around the turbine 338. The wall 336 fluidically separates the irrigation flow path 332 into an irrigation inflow path 331 and an irrigation outflow path 333. Flow of irrigation fluid 340 through the irrigation flow path 332 powers the flow-to-rotary converter 338 in two directions. Flow of irrigation fluid 340 through the irrigation inflow path 331 from the irrigation connection 315 and the second end 313 towards the irrigation outlet 314 and the first end 311 powers the flow-to-rotary converter 338. Flow of irrigation fluid 340 through the irrigation outflow path 333 from the first end 311 towards an irrigation recovery outlet 323 and the second end 313 powers the flow-to-rotary converter 338. Irrigation fluid 340 flows out of the irrigation recovery outlet 323 and into an irrigation recovery connection 321 for recovery and disposal. Irrigation inlet 318 and aspiration outlet 319 are depicted.

The irrigation outlet 314 may be located in the flow path 332 proximate the first end 311. The irrigation outlet 314 may be located proximate a portion of the irrigation flow path 332 at which the irrigation flow path 332 transitions between the irrigation inflow path 331 and the irrigation outflow path 333.

An aspiration flow conduit 370 provides an aspiration flow path separately from the body 312. The aspiration connection 317 may be connected with the aspiration flow conduit 370 and the aspiration outlet 316 for supplying negative pressure to the apparatus 10 to balance delivery of irrigation fluid to the capsular space and to recover aspirated fluid from the capsular space. The aspiration outlet 316 may be located on the aspiration flow conduit 370 proximate the first end 311. The aspiration outlet 316 and the aspiration flow conduit 370 may be located on the body 312 separate from the irrigation outlet 314 along the height 307. The sweeper head 320 includes the sweeper arms 322 and the tapered ends 324. The sweeper head 320 may be located proximate the irrigation outlet 314. The sweeper head 320 may be located across the height 307 from the aspiration outlet 316 and proximate the aspiration outlet 316 along the length 305.

Figure 15:
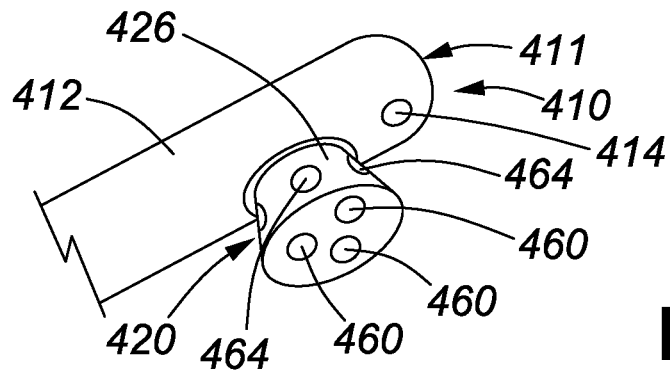
FIG. 15 is a perspective schematic of a capsular space clearing apparatus.

FIG. 15 shows an apparatus 410. The apparatus 410 including a sweeper head 420 proximate the first end 411 and the irrigation outlet 414. The sweeper head 420 includes the hub 426 and distal sweeper surfaces 460 located at a portion of the hub 426 distal from the body 412 for sweeping the posterior surface of the lens capsule as shown in FIG. 10.

Any suitable number of distal sweeper surfaces 462 may be included on the hub 426, (e.g. the three sweeper surfaces 462 in the apparatus 410, four sweeper surfaces 662 in the apparatus 610, etc.). Lateral sweeper surfaces 464 are provided for sweeping the anterior leaf of a capsule as shown in FIG. 9. Any suitable number of lateral sweeper surfaces 464 may be included on the hub 426, (e.g. four lateral sweeper surfaces 464 in the apparatus 410, two lateral sweeper surfaces 664 in the apparatus 610, etc.). The distal sweeper contact surfaces 462 and lateral sweeper contact surfaces 464 may each be flush with the hub 426 or protrude from the hub 426.

Figure 16:
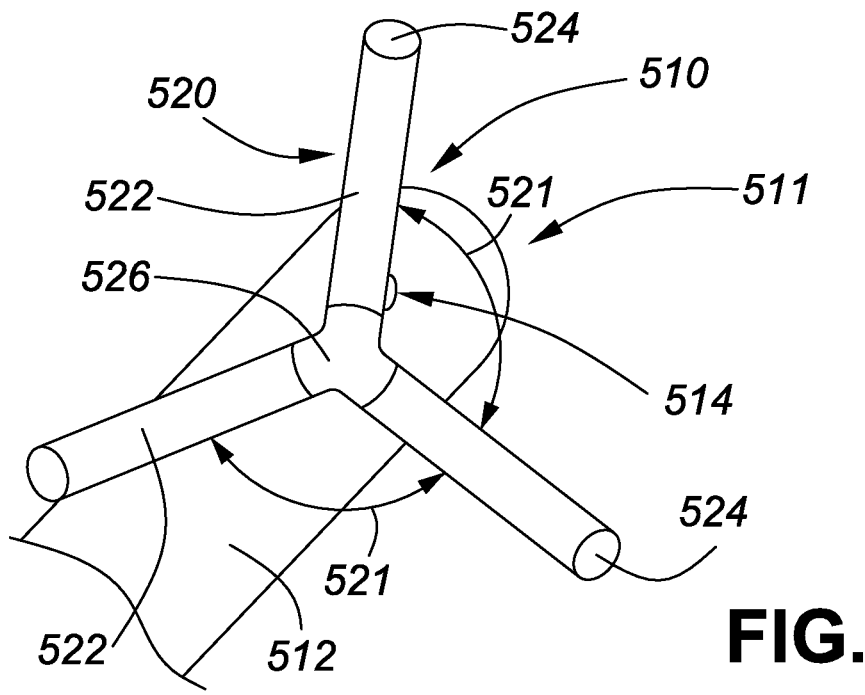
FIG. 16 is a bottom plan view schematic of a capsular space clearing apparatus.

FIG. 16 shows an apparatus 510. The sweeper head 520 and the irrigation outlet 514 are proximate the first end 511. The sweeper head 520 includes the hub 526 and three arms 522 extending from the hub 526 and ending in the tapered ends 524. The arms 522 may be evenly separated from each other by the angle 521. Similarly as compared with the apparatus 10, any suitable number of arms may be included, with the apparatus 510 and the apparatus 10 providing two specific examples having two arms 22 and three arms 522, respectively.

Figure 17:
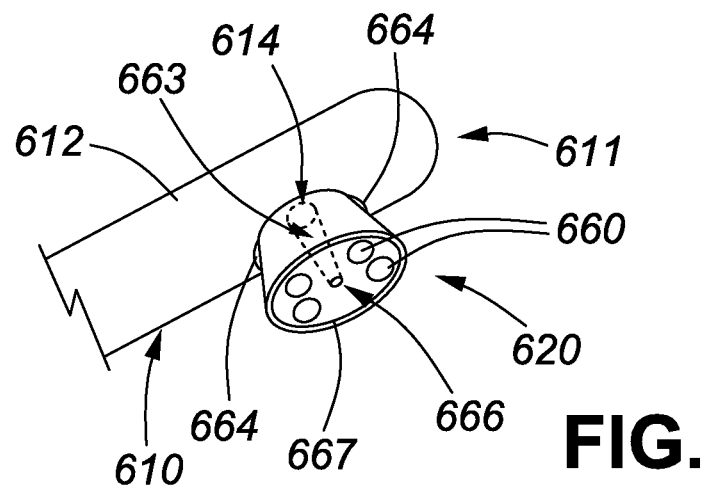
FIG. 17 is a perspective schematic of a capsular space clearing apparatus.

FIG. 17 shows an apparatus 610. The sweeper head 620 includes the hub 626 proximate the first end 611. The hub 626 includes distal sweeper surfaces 662 located at a portion of the hub 626 distal from the body 612. The hub 626 includes the distal sweeper surfaces 662 and the lateral sweeper surfaces 664. The distal sweeper surfaces 662 and lateral sweeper surfaces 664 may each be flush with the hub 626 or protrude from the hub 626. The hub 626 includes a sweeper head outlet 666 and a sweeper head channel 663 in fluid communication with the irrigation outlet 614 for providing irrigation fluid externally to the body 612 through the sweeper head outlet 662 in the hub 626. The hub 626 includes a boundary sweeper surface 667 extending around an outer of the hub 626. Where the hub 626 has a circular shape, the boundary sweeper surface 667 may extend around a circumference of the hub 626. The boundary sweeper surface 667 may extend from an outer and distal portion of the hub 626. The boundary sweeper surface 667 may contact the anterior leaf and other portions of the lens capsule anterior to the equator when the apparatus 612 is located in the anterior position, as shown for the apparatus 10 in FIG. 9. The boundary sweeper surface 667 may contact the posterior surface of the lens capsule and other portions of the lens capsule posterior to the equator when the apparatus 612 is located in the posterior position, as shown for the apparatus 10 in FIG. 10.

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art without departing from the scope, which is defined solely by the claims appended hereto.

What is claimed is:

1. A capsular sweeper apparatus comprising:
    a body extending along a length between a first end and a second end;
    an irrigation inlet for receiving irrigation fluid into the body;
    an irrigation outlet proximate the first end and in fluid communication with the irrigation inlet for providing irrigation fluid externally to the body;

an aspiration inlet proximate the first end for receiving aspirated fluid into the apparatus;

an aspiration outlet in fluid communication with the aspiration inlet for removing aspirated fluid from the apparatus;

a sweeper head rotatably connected with the body, wherein the sweeper head comprises a hub and at least two arms extending from the sweeper hub defining a sweeper surface for contacting an ocular capsule during rotation of the sweeper head, wherein the at least two arms are in a v-shaped configuration and are separated by an angle of between 120° and 150°;

a flow-to-rotary converter engaged with the sweeper head and located within the body for converting flow velocity into rotation velocity to rotate the sweeper head, wherein the flow-to-rotary converter is located within an irrigation flow path defined in the body between the irrigation inlet and the irrigation outlet for converting flow velocity of fluid in the irrigation flow path into rotation velocity to rotate the sweeper head, wherein the flow-to-rotary converter comprises a turbine; and a wall within the body for fluidically isolating the irrigation flow path from an aspiration flow path defined in the body between the aspiration inlet and the aspiration outlet and wherein the flow-to-rotary converter is located in the body in fluid communication with the irrigation flow path and not with the aspiration flow path.

2. The apparatus of claim 1 wherein the irrigation outlet is separated from the aspiration inlet along a height perpendicular to the length.

3. The apparatus of claim 2 wherein the irrigation outlet is opposite the aspiration inlet along the height.

4. The apparatus of claim 1 wherein the irrigation outlet is proximate the sweeper head along the length.

5. The apparatus of claim 1 wherein the irrigation outlet is proximate to the sweeper head along a height perpendicular to the length.

6. The apparatus of claim 1 wherein the irrigation outlet is defined on a portion of the body overlapping with the sweeper head and in fluid communication with a channel defined in the sweeper head and a sweeper head outlet defined on the sweeper head.

7. The apparatus of claim 1 wherein the irrigation outlet is separated from the sweeper head along the length and proximate the sweeper head along a height perpendicular to the length.

8. The apparatus of claim 7 wherein the aspiration inlet is opposite the irrigation outlet along the height.

9. The apparatus of claim 1 wherein the aspiration inlet is defined in the body for receiving the aspirated fluid into the body and the aspiration outlet is defined in the body for removing aspirated fluid from the body.

10. The apparatus of claim 1 further comprising an aspiration flow conduit connected with and fluidically isolated from the body, and wherein the aspiration inlet is defined in the aspiration flow conduit for receiving the aspirated fluid into the aspiration flow conduit and the aspiration outlet is defined in the aspiration flow conduit for removing aspirated fluid from the aspiration flow conduit.

11. The apparatus of claim 1 wherein the aspiration inlet is proximate to the sweeper head along a height perpendicular to the length.

12. The apparatus of claim 1 wherein the at least two arms extend from a portion of the hub distal from the body.

13. The apparatus of claim 1 wherein the at least two arms extend from a lateral portion of the hub.

14. The apparatus of claim 1 wherein the at least two arms extend from an outer distal portion of the hub.

15. The apparatus of claim 1 wherein a cross-sectional surface area of the aspiration flow path is greater than a cross-sectional area of the irrigation flow path for mitigating limitation of flow into the body at the aspiration inlet and clogging of the apparatus.

16. The apparatus of claim 1 further comprising an aspiration flow conduit connected with the body and fluidically isolated from the irrigation flow path, and wherein the aspiration inlet is defined in the aspiration flow conduit for receiving the aspirated fluid into the aspiration flow conduit and the aspiration outlet is defined in the aspiration flow conduit for removing aspirated fluid from the aspiration flow conduit.

17. The apparatus of claim 1 wherein a cross-sectional surface area of the aspiration inlet is greater than a cross-sectional area of the irrigation flow path for mitigating limitation of flow into the body at the aspiration inlet and clogging of the apparatus.

18. The apparatus of claim 1, wherein the wall is curved away from the irrigation flow path and into the aspiration flow path to form a curved recess facing the irrigation flow path in which the turbine is partially accommodated.

19. The apparatus of claim 1, wherein the at least two arms have tapered ends.

20. The apparatus of claim 1, wherein the at least two arms are semi-rigid.

21. The apparatus of claim 1, wherein the at least two arms extend about 5 mm from the hub.

* * * * *